(12) United States Patent
McNabb et al.

(10) Patent No.: US 6,376,422 B1
(45) Date of Patent: Apr. 23, 2002

(54) DEHYDROGENATION CATALYSTS AND METHODS

(75) Inventors: Andrew J. McNabb, Lake Jackson; Karen A. Lewno, Angleton; R. Merritt Sink, Lake Jackson, all of TX (US)

(73) Assignee: BASF Corporation, Mount Olive, NJ (US)

( * ) Notice: Subject to any disclaimer, the term of this patent is extended or adjusted under 35 U.S.C. 154(b) by 0 days.

(21) Appl. No.: 09/794,397

(22) Filed: Feb. 28, 2001

(51) Int. Cl.⁷ .......................... B01J 31/00; B01J 23/00; B01J 37/00; C07C 45/00; C07C 49/105
(52) U.S. Cl. .................. 502/307; 502/103; 502/117; 502/319; 568/360; 568/361; 568/376
(58) Field of Search ................. 502/103, 117, 502/307, 319; 568/360, 361, 376

(56) References Cited

U.S. PATENT DOCUMENTS

| | | | |
|---|---|---|---|
| 2,640,084 A | 5/1953 | Chitwood et al. | |
| 3,987,112 A | 10/1976 | Lyons | 260/621 |
| 3,998,884 A | 12/1976 | Gibson | 260/586 |
| 4,310,703 A | 1/1982 | Tamaru et al. | 568/361 |
| 4,380,673 A | 4/1983 | Bournonville et al. | 568/361 |
| 4,417,076 A | 11/1983 | Rozovsky et al. | 568/361 |
| 4,599,454 A | 7/1986 | Elliott et al. | 568/387 |
| 4,670,605 A | 6/1987 | Chiu et al. | 568/361 |
| 4,764,498 A * | 8/1988 | Wissner et al. | 502/251 |
| 4,918,239 A | 4/1990 | Wang et al. | 568/360 |
| 5,900,482 A * | 5/1999 | Teramoto et al. | 540/535 |

* cited by examiner

Primary Examiner—Samuel Barts
Assistant Examiner—Elvis O. Price
(74) Attorney, Agent, or Firm—Nixon & Vanderhye P.C.

(57) ABSTRACT

Catalyst mixtures are comprised of zinc oxide, calcium carbonate or calcium oxide, and an amount of chromium (III) oxide in an amount sufficient to improve conversion and/or selectivity of cyclohexanol to cyclohexanone under cyclohexanol dehydrogenation conditions.

18 Claims, No Drawings

DEHYDROGENATION CATALYSTS AND METHODS

FIELD OF THE INVENTION

The present invention relates generally to dehydrogenation catalysts and to catalytic dehydrogenation reactions employing the same. In preferred forms, the present invention relates to catalysts employed in dehydrogenation of cyclohexanol to produce cyclohexanone.

BACKGROUND AND SUMMARY OF THE INVENTION

It is well known that cyclohexanol can be catalytically dehydrogenated to produce cyclohexanone, as evidenced, for example, by U.S. Pat. No. 2,640,084.[1] In this regard, various catalysts have been proposed for such catalytic dehydrogenation processes. For example, in the above-cited U.S. '084 patent, a nickel dehydrogenation catalyst is proposed having copper (mostly in the form of copper metal) and chromium (mostly in the form of its oxide) which has been stabilized by the presence of an alkali metal sulfate. U.S. Pat. No. 4,310,703 discloses that a copper-chromium catalyst derived from a mixture of copper oxide and chromium oxide can be employed in the catalytic dehydrogenation of cyclohexanol to form cyclohexanone. Furthermore, U.S. Pat. No. 4,417,076 notes that a mixture of nickel with a promoter (e.g., germanium and/or lead) is usefully employed in the dehydrogenation of cyclohexanes into their corresponding cyclic ketones. Catalytic mixtures of copper oxide and zinc oxide for dehydrogenation of cyclohexanol to form cyclohexanone are suggested by U.S. Pat. Nos. 4,918,239 and 4,670,605.

[1] The entire contents of this, and all other, publications hereinafter cited are expressly incorporated hereinto by reference.

While various catalysts for dehydrogenation processes to convert cyclohexanol to cyclohexanone are known generally, there still exists a need to provide catalysts with superior conversion and selectivity properties. It is towards fulfilling such a need that the present invention is directed.

Broadly, the present invention is embodied in dehydrogenation catalysts and catalytic dehydrogenation processes using the same. The catalysts of the present invention more specifically is embodied in catalyst mixtures comprised of zinc oxide (ZnO), calcium carbonate ($CaCO_3$) or calcium oxide (CaO), and an amount of chromium (III) oxide ($Cr_2O_3$) in an amount sufficient to improve conversion and/or selectivity of cyclohexanol to cyclohexanone under cyclohexanol dehydrogenation conditions.

These and other aspects and advantages will become more apparent after careful consideration is given to the following detailed description of the preferred exemplary embodiments thereof.

DETAILED DESCRIPTION OF THE INVENTION

The catalysts of the present invention will necessarily include zinc oxide, calcium carbonate or calcium oxide and chromium (III) oxide. The zinc oxide is most preferably present in the catalysts of the present invention in amounts ranging between about 45 wt. % to about 60 wt. %, and more preferably in an amount of about 55 wt. % (+/− about 5 wt. %).

The calcium carbonate or calcium oxide may be included in the catalysts of the present invention in amounts ranging between about 25 wt. % to about 45 wt. %, and more preferably between about 30 wt. % to about 35 wt. % (+/− about 5 wt. %). The catalysts of the present invention may be formulated initially to include calcium carbonate, with the catalyst being controllably heated to convert the calcium carbonate to calcium oxide prior to being placed in service.

Chromium (III) oxide ($Cr_2O_3$) is present in the catalysts of the present invention in amounts sufficient to improve conversion and/or selectivity of cyclohexanol to cyclohexanone under cyclohexanol dehydrogenation conditions. The chromium (III) oxide is present in amounts ranging from about 0.2 wt. % to about 30 wt. %, more preferably 1.5 wt. % to about 20 wt. %, and most preferably between about 2.5 wt. % and 15 wt. %.

The catalysts of the present invention may include other optional constituents that are typically employed in dehydrogenation purposes. For example, the catalysts of the present invention most preferably include sodium oxide (NaO) in an amount between about 0.1 to about 3.0 wt. %, and more typically in an amount of about 0.5 wt. % to about 1.5 wt. %.

The catalysts of the present invention will typically exhibit bulk densities of between about 700 g/l to about 1250 g/l, porosities of between about 0.10 to about 0.35 $cm^3/g$, and a hardness ($kg_f$) of between about 8.0 to about 15.0.

In use, the catalysts of the present invention will be placed in a suitable dehydrogenation reaction vessel which is supplied with a cyclohexanol-containing feed stream under conventional dehydrogenation conditions. The cyclohexanol in the feed stream will thereby be dehydrogenated to form cyclohexanone according to known reaction mechanisms.

The present invention will be further understood from the following non-limiting Examples.

EXAMPLES

Example 1

Dehydrogenation catalysts having the compositions as noted below in Table I were made and tested in a laboratory scale dehydrogenation reactor using a feedstock comprised mainly of cyclohexanol (greater than about 90%). Each catalyst was subject to cyclohexanol conversion conditions to achieve vapor outlet temperatures of 290° C., 300° C., 310° C. and 320° C. The average conversions, average selectivity towards cyclohexanone and the cyclohexanone product factor (i.e., the factor which indicates the potential for increased dehydrogenation production capacity and is obtained by the product of the conversion and selectivity) was evaluated for each catalyst at each such vapor outlet temperature appears in Tables II through IV below, respectively.

TABLE I

Catalyst Compositions

| Component (Wt. %) | 2.5 Cr (Invention) | 5 Cr (Invention) | 15 Cr (Invention) | 0 Cr (Control) |
|---|---|---|---|---|
| ZnO | 53.8 | 57 | 55.4 | 55.0 |
| $Cr_2O_3$ | 2.5 | 5.5 | 14.7 | 0 |
| $CaCO_3$ | 43.5 | 34.6 | 26.5 | 45.0 |
| $Na_2O$ | 0.6 | 1.3 | 1.5 | 0.5 |

TABLE II

Avg. Cyclohexanone Conversions

| Vapor Outlet Temp. (° C.) | Catalyst Identification | | | |
|---|---|---|---|---|
| | 2.5 Cr (Invention) | 5 Cr (Invention) | 15 Cr (Invention) | 0 Cr (Control) |
| 290 | 72.3 | 52.4 | 63.8 | 40.6 |
| 300 | 72.5 | 66.2 | 68.4 | 47.8 |
| 310 | 81.8 | 79.3 | 72.3 | 51.2 |
| 320 | 87.3 | 85.4 | 84.7 | 63.2 |

TABLE III

Avg. Selectivity Towards Cyclohexanone

| Vapor Outlet Temp. (° C.) | Catalyst Identification | | | |
|---|---|---|---|---|
| | 2.5 Cr (Invention) | 5 Cr (Invention) | 15 Cr (Invention) | 0 Cr (Control) |
| 290 | 97.4 | 99.3 | 97.5 | 99.4 |
| 300 | 99.0 | 98.7 | 99.2 | 99.2 |
| 310 | 98.9 | 98.8 | 98.9 | 99.1 |
| 320 | 98.5 | 98.6 | 98.6 | 99.0 |

TABLE IV

Cyclohexanone Product Factor

| Vapor Outlet Temp. (° C.) | Catalyst Identification | | | |
|---|---|---|---|---|
| | 2.5 Cr (Invention) | 5 Cr (Invention) | 15 Cr (Invention) | 0 Cr (Control) |
| 290 | 0.70 | 0.53 | 0.62 | 0.40 |
| 300 | 0.72 | 0.65 | 0.68 | 0.47 |
| 310 | 0.81 | 0.78 | 0.72 | 0.51 |
| 320 | 0.86 | 0.84 | 0.84 | 0.63 |

As can be seen from the data in Table II, at all of the catalyst evaluation conditions, the chromium catalysts achieved conversions that were substantially higher than the Control catalyst. The conversions obtained with the 2.5Cr catalyst were slightly higher than the conversions obtained with the 5Cr and 15Cr catalysts.

The data in Table III demonstrate that three of the four selectivities obtained with the 2.5Cr catalyst were higher than a target 98% selectivity. Also, the selectivities obtained with the 2.5Cr catalyst were slightly lower than the selectivities obtained with the Control and were approximately the same as the selectivities obtained with the 5Cr and 15Cr catalysts.

The data of Table IV indicate that it may be possible to substantially increase the production capacity of dehydrogenation reactors by the addition of chromium to a conventional ZnO catalyst. In this regard, all of the chromium-containing catalysts achieved higher product factors at all of the temperatures evaluated when compared to the baseline case. The product factors obtained with the 2.5Cr catalyst were slightly higher than the product factors obtained with the 5Cr and 15Cr catalysts.

Example 2
(Comparative)

A mixture containing approximately 91.9% cyclohexanol was continuously fed into a laboratory reactor containing a catalyst consisting of approximately 55% zinc oxide and 45% calcium carbonate. The conversion of cyclohexanol into cyclohexanone was measured and determined to average 40.6% at a reaction temperature of 290° C.

Example 3

A mixture containing approximately 87.8% cyclohexanol was continuously fed into a laboratory reactor containing a catalyst consisting of approximately 55% zinc oxide, 30% calcium carbonate and 15% chromium oxide. The conversion of cyclohexanol into cyclohexanone was measured and determined to average 63.8% at a reaction temperature of 290° C.

Example 4
(Comparative)

A mixture containing approximately 89.9% cyclohexanol was continuously fed into a laboratory reactor containing a catalyst consisting of approximately 70% zinc oxide and 30% calcium carbonate. The conversion of cyclohexanol into cyclohexanone was measured and determined to average 42.0% at a reaction temperature of 290° C.

Example 5
(Comparative)

A mixture containing approximately 92.1% cyclohexanol was continuously fed into a laboratory reactor containing a catalyst consisting of approximately 55% zinc oxide and 45% calcium carbonate. The conversion of cyclohexanol into cyclohexanone was measured and determined to average 47.8% at a reaction temperature of 300° C.

Example 6

A mixture containing approximately 92.2% cyclohexanol was continuously fed into a laboratory reactor containing a catalyst consisting of approximately 55% zinc oxide, 30% calcium carbonate and 15% chromium oxide. The conversion of cyclohexanol into cyclohexanone was measured and determined to average 68.4% at a reaction temperature of 300° C.

Example 7
(Comparative)

A mixture containing approximately 89.9% cyclohexanol was continuously fed into a laboratory reactor containing a catalyst consisting of approximately 70% zinc oxide and 30% calcium carbonate. The conversion of cyclohexanol into cyclohexanone was measured and determined to average 51.5% at a reaction temperature of 300° C.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A cyclohexanol dehydrogenation catalyst comprising a mixture of zinc oxide, calcium carbonate and/or calcium oxide, and an amount of chromium (III) oxide in an amount of from about 0.2 wt. % to about 30 wt. % sufficient to improve conversion and/or selectivity of cyclohexanol to cyclohexanone under cyclohexanol dehydrogenation conditions.

2. The catalyst of claim 1, wherein the zinc oxide is present in an amount of between about 45 wt. % to about 60 wt. %.

3. The catalyst of claim 2, wherein the zinc oxide is present in an amount of about 55 wt. % (+/− about 5 wt. %).

4. The catalyst of claim 1, wherein the calcium carbonate is present in an amount between about 25 wt. % to about 45 wt. %.

5. The catalyst of claim 4, wherein the calcium carbonate and/or calcium oxide is present in an amount between about 30 wt. % to about 35 wt. % (+/− about 5 wt. %).

6. The catalyst of claim 1, wherein the chromium (III) oxide is present in an amount between about 2.5 wt. % and 15 wt. %. wt. % (+/− about 5 wt. %).

7. The catalyst of claim 1, further comprising between about 0.1 to about 3.0 wt. % of sodium oxide.

8. A cyclohexanol dehydrogenation catalyst comprising a mixture of about 55 wt. % (+/− 5 wt. %) zinc oxide, about 35 wt. % (+/− 5 wt. %) calcium carbonate and/or calcium oxide, and between about 0.2 wt. % to about 30 wt. % of chromium (III) oxide.

9. A method for the catalytic dehydrogenation of cyclohexanol comprising bringing a cyclohexanol-containing feed stream under dehydrogenation conditions into contact with a dehydrogenation catalyst mixture comprised of zinc oxide, calcium carbonate and/or calcium oxide, and an amount of chromium (III) oxide from about 0.2 wt. % to about 30 wt. % sufficient to improve conversion and/or selectivity of cyclohexanol to cyclohexanone for a time sufficient to convert the cyclohexanol in the feed stream to cyclohexanone.

10. The method of claim 9, wherein the zinc oxide is present in an amount of between about 45 wt. % to about 60 wt. %.

11. The method of claim 10, wherein the zinc oxide is present in an amount of about 55 wt. % (+/− about 5 wt. %).

12. The method of claim 9, wherein the calcium carbonate is present in an amount between about 25 wt. % to about 45 wt. %.

13. The method of claim 12, wherein the calcium carbonate and/or calcium oxide is present in an amount between about 30 wt. % to about 35 wt. % (+/− about 5 wt. %).

14. The method of claim 9, wherein the chromium (III) oxide is present in an amount between about 2.5 wt. % and 15 wt. %.

15. The method of claim 9, further comprising between about 0.1 to about 3.0 wt. % of sodium oxide.

16. The method of claim 9, wherein the cyclohexanol dehydrogenation catalyst comprises a mixture of about 55 wt. % (+/− 5 wt. %) zinc oxide, about 35 wt. % (+/− 5 wt. %) calcium carbonate and/or calcium oxide, and between about 0.2 wt. % to about 30 wt. % of chromium (III) oxide.

17. A cyclohexanol dehydrogenation catalyst mixture consisting of (i) about 55 wt. % (+/− 5 wt. %) zinc oxide, (ii) about 35 wt. % (+/− 5 wt. %) calcium carbonate and/or calcium oxide, and (iii) an amount between about 0.2 wt. % to about 30 wt. % of chromium (III) oxide sufficient to improve conversion and/or selectivity of cyclohexanol to cyclohexanone.

18. The cyclohexanol dehydrogenation catalyst mixture of claim 17, which further consists of (iv) between about 0.1 to about 3.0 wt. % sodium oxide.

* * * * *